(12) United States Patent
O'Mahony et al.

(10) Patent No.: US 8,556,846 B2
(45) Date of Patent: Oct. 15, 2013

(54) BLOOD VOLUME CONTROLLER DURING FLUID REMOVAL

(75) Inventors: John J. O'Mahony, Maple Grove, MN (US); Paul A. Sobotka, West St. Paul, MN (US); Edward G. Rychlick, Maple Grove, MN (US)

(73) Assignee: Gambro UF Solutions, Inc., Brooklyn Park, MN (US)

( * ) Notice: Subject to any disclaimer, the term of this patent is extended or adjusted under 35 U.S.C. 154(b) by 350 days.

(21) Appl. No.: 11/460,322

(22) Filed: Jul. 27, 2006

(65) Prior Publication Data

US 2007/0055198 A1 Mar. 8, 2007

Related U.S. Application Data

(60) Provisional application No. 60/703,015, filed on Jul. 28, 2005.

(51) Int. Cl.
*A61M 31/00* (2006.01)

(52) U.S. Cl.
USPC .......... 604/67; 604/31; 604/65; 604/66; 604/503; 604/506; 604/507; 604/508

(58) Field of Classification Search
USPC .......... 604/65–67, 503, 506, 507, 508, 31
See application file for complete search history.

(56) References Cited

U.S. PATENT DOCUMENTS

| 4,080,966 A * | 3/1978 | McNally et al. ........... 604/505 |
| 5,984,893 A * | 11/1999 | Ward ........................ 604/131 |
| 6,582,656 B1 * | 6/2003 | Steuer et al. ............... 422/44 |
| 6,623,470 B2 * | 9/2003 | Munis et al. ............... 604/503 |
| 6,681,128 B2 * | 1/2004 | Steuer et al. ............... 600/322 |
| 2006/0052764 A1 * | 3/2006 | Gelfand et al. ............. 604/500 |

OTHER PUBLICATIONS

John M. McCurley, MD, et al, "Furosemide and the progression of Left Ventricular Dysfunction in Experimental Heart Failure", Journal of the American College of Cardiology, vol. 44, No. 6, Sep. 15, 2004, pp. 1301-1307.

Michael Domanski, MD et al., Diuretic use, Progressive Heart Failure, and Death in Patients in the Studies of Left Ventricular Dysfunction (SOLVD), Journal of the American College of Cardiology, vol. 42, No. 4, Aug. 20, 2003, pp. 705-708.

Howard A. Cooper MD et al, "Diuretics and Risk of Arrhythmic Death in Patients With Left Ventricular Dysfunction", http://www.circulationaha.org, Sep. 2, 1999, pp. 1311-1315.

Gerald W. Neuberg, MD et al, "Diuretic Resistance Predicts Mortality in Patients With Advanced Heart Failure", American Heart Journal, Jul. 2002, pp. 31-38.

(Continued)

*Primary Examiner* — Bhisma Mehta
*Assistant Examiner* — Larry R Wilson
(74) *Attorney, Agent, or Firm* — Nixon & Vanderhye P.C.

(57) ABSTRACT

A blood volume control method has been developed including: monitoring a condition of a patient (such as hematocrit (Hct)), wherein the condition is indicative of blood volume in the patient; automatically determining that the condition indicates a low blood volume in the patient; automatically infusing an infusion solution into the patient in response to the determination of a low blood volume, and automatically adjusting the infusion to maintain the monitored condition at a predetermined value.

19 Claims, 4 Drawing Sheets

(56) References Cited

OTHER PUBLICATIONS

Gary S. Francis MD, et al., "Comparison of Neuroendocrine Activation in Patients With Left Ventricular Dysfunction With and Without Congestive Heart Failure, A Substudy of the Studies of Left Ventricular Dysfunction (SOLVD)", Neuroendocrine Activity and Heart Failure, Circulation 1990, pp. 1724-1729.

Charles L. Emerman et al, "Impact of Intravenous Diuretics on the Outcomes of Patients Hospitalized With Acute Decompensated Heart Failure: Insights from the ADHERE® Registry", Journal of Cardiac Failure, vol. 10, No. 4, Suppl. 2004, p. 368.

Gary S. Francis MD, et al., Acute Vasoconstrictor Response to Intravenous Furosemide in Patients With Chronic Congestive Heart Failure, Activation of the Neurohumoral Axis, Annals of Internal Medicine, Jul. 1985, vol. 103, No. 1, pp. 1-6.

Stephen S. Gottlieb, MD, et al., "BG9719 (CVT-124), an A1 Adenosine Receptor Antagonist, Protects Against the Decline in Renal Function Observed With Diuretic Therapy", http://www.circulationaha.org, 2002, pp. 1348-1353.

John Bayliss et al., Untreated Heart Failure: Clinical and Neuroendocrine Effects of Introducing Diuretics, 1987, pp. 17-22.

Javed Butler MD, et al., Relationship Between Heart Failure Treatment and Development of Worsening Renal Function Among Hospitalized Patients, American Heart Journal, Feb. 2004, pp. 331-338.

Mark S. Weinfeld MD, et al, "Aggravated Renal Dysfunction During Intensive Therapy for Advanced Chronic Heart Failure", American Heart Journal, Aug. 1999, pp. 285-290.

* cited by examiner

BLOOD VOLUME CONTROLLER DURING FLUID REMOVAL

This application claims the benefit of U.S. Provisional Application Ser. No. 60/703,015 filed Jul. 28, 2005, the entirety of which is incorporated by reference.

BACKGROUND

The present invention is directed to an apparatus and system for preventing hypotension during aggressive diuretic therapy.

Heart failure is a common cause of hospitalization among Medicare beneficiaries and is associated with significant morbidity and mortality. Most patients hospitalized with heart failure have symptoms of congestion due to excess fluid retention. CHF (chronic heart failure) is a salt-avid state, where salt (Na) retention is based on an activation of the circulating RAAS (renin-angiotensin-aldosterone system) with consequent expansion of intravascular and extravascular volume resulting in the signs and symptoms of CHF. Loop diuretics which often are successful in generating a rapid diuresis and mild natriuresis and have become the basis of treatment of congestion. Loop diuretics have become the primary treatment for fluid overload in patients with heart failure and are used in 88% of patients hospitalized for heart failure.

Concerns about the safety of diuretic based treatment strategies for congestive heart failure have been raised. (Weber et al Am Coll Cardiol. 2004 Sep. 15;44(6):1301-7., Domanski et al Am Coll Cardiol. 2003 Aug. 20;42(4):705-8, Cooper et al Circulation. 1999 Sep. 21;100(12):1311-5, Neuberg et al Am Heart J. 2002 Jul;144(1):31-8, Francis et al Circulation. 1990 Nov;82(5):1724-9, Emerman C, et al. Heart Failure Society of America 2004 Annual Scientific Meeting; Sep. 12-15, 2004; Toronto, ON.). Deleterious hemodynamic effects of aggressive loop diuretic strategies have long been appreciated, including acute decreases of cardiac output, increases in pulmonary capillary wedge pressure and total systemic vascular resistance have been documented (Francis AIM 1985; 103:1-6). Aggressive diuretic treatment strategies are associated with decreasing renal function, as documented by reductions of both renal blood flow and glomerular filtration rates. (Gottlieb SS et al. Circulation. 2002;105:1348-1353). This deleterious effect of acute diuretic administration may be the proximate cause of worsening renal function observed in the setting of diuretic therapy. An increase of Serum Creatinine (sCr) of >0.3 mg/dl, occurs in nearly ⅓ of hospitalized heart failure patients [Butler AHJ 2004]. Progressive azotemia in this setting is associated with increase length of stay in the hospital and worse prognosis. [Butler AHJ 2004, Weinfeld AHJ 1999].

Activation of the neurohormonal system consequent to diuretic administration is associated with the observed reductions of cardiac and renal function. (Bayliss Br Heart J, 1987; 57:17-22). In addition to the renin-angiotensin-aldosterone activation associated with diuretic use, the direct renal loss of cations Ca and Mg following loop diuretics, result in stimulation of PTH release; this has been hypothesized to be linked to the long term morbidity and mortality associated with diuretic reliance in treatment strategies for CHF.(K Weber, et al). The ACC/AHA Guidelines for the Evaluation and Management of Chronic Heart Failure in the Adult,© 2001 by the American College of Cardiology and the American Heart Association, Inc. state that the "Appropriate use of diuretics is a key element in the success of other drugs used for the treatment of HF. The use of inappropriately low doses of diuretics will cause fluid retention, which can diminish the response to ACE inhibitors and increase the risk of treatment with beta-blockers. Conversely, the use of inappropriately high doses of diuretics will lead to volume contraction, which can increase the risk of hypotension with ACE inhibitors and vasodilators and the risk of renal insufficiency with ACE inhibitors and angiotensin II receptor antagonists. Optimal use of diuretics is the cornerstone of any successful approach to the treatment of HF.".

Beyond the concerns about the safety of loop diuretic based congestion strategies, the therapeutic efficacy of this strategy is questionable, nearly half of patients hospitalized for heart failure have less than 5 pounds of weight loss at the time of discharge [ADHERE] thus, the current treatment strategies, principally using diuretics to treat congestion related to heart failure, are largely ineffective in weight reduction. Diuretic resistance, defined as relative or absolute loss of diuresis following administration of potent loop diuretics is common. Moreover, the braking phenomenon, reduced efficacy of Na removal with each loop diuretic dose, results in attenuated efficacy of sodium removal when treatment strategies are based on loop diuretics.

Diuretic dosage is limited by the open loop nature of the drug delivery process so clinicians have to be aware of the potential for hypotension resulting in poor renal perfusion, an increase in GFR, activation of the RAAS system and the resultant poor perfusion of the kidney. It is believed that many of the deleterious effects of diuretics stem from aggressive volume depletion and that the viscous cycle can be overcome if this volume depletion is prevented. When a diuretic is administered fluid is recruited directly from the vascular volume via the kidney and if this rate exceeds the rate that the resultant oncotic pressure can recruit fluid from the interstitial space the volume in the vascular space is depleted. This replenishment rate is known as the PRR (Plasma Refill Rate). Once the diuretic is delivered to the patient, clinicians have no way to titrate its effect, thus in the event that hypotension ensues, a isotonic solution is administered to the patient intravenously to replenish the vascular volume and the patients is left to stabilize before continuing therapy. This is the current mode of practice, because no better alternative have been found. Much of the literature talks about ways of optimizing diuretic dosage accounting for the pharmakinetics of the drug and monitoring output. In clinical practice this translates to a doubling of the dose protocol over given time periods based upon measured urine output.

Hypotension is the manifestation of hypovolumea or a severe fluid misbalance. Symptomatically, hypotension may be experienced by the patient first as light-headedness. To monitor patients for hypotension, non-invasive blood pressure monitors (NIBP) are commonly used during renal replacement therapy (RRT). When detected early, hypotension resulting from the excessive loss of fluid is easily reversed by giving the patient intravenous fluids.

SUMMARY

There is a long felt need for a method to improve response by patients to diuretics so as to enable the kidneys' response to the diuretic to match exactly the plasma refill rate. This would prevent the depletion of blood volume and thus hypotension during diuretic delivery making the process simpler and faster, and reducing the guess work of diuretic titration. Clinicians could focus on the patients urine output and net fluid loss instead of worrying about the effect of the diuretic dosage. This can be achieved by monitoring the patient's blood volume and replenishing drops in blood volume by infusing the net loss with an equivalent infusion solution volume. Blood volume may be measured directly or a surrogate of blood volume may be used. Examples of surrogates of blood volume include absolute or difference measures of blood constituent such as hematocrit, oncotic pressure, hemoglobin, injected dye concentration, electrical resistance and impedance or protein concentration.

Hct (hematocrit) is a surrogate of blood volume. By continuously monitoring this parameter, blood volume depletion as a result of over diuresis can be eliminated by infusing a replenishment solution to the vascular volume in response to an increase in Hct avoiding vascular volume contraction. The infusion solution controller targets the base Hct of the patient before the initiation of therapy or some other desired Hct target. The replenishment solution is infused into the patients vascular volume when the Hct reading rises above the predefined target. The base Hct may be defined as the Hct before the initiation of therapy and/or before any vascular volume depletions occur. If the Hct target is less than the base Hct, the vascular volume will be increased. If the Hct target is higher than the base Hct, the vascular volume will be decreased The net fluid removed from the patient is the summation of urine volume minus the volume of replenishment solution delivered. An advantage of such a system is that the resultant net fluid removed from the patient will exactly match the patients' plasma refill rate preventing hypotension. It also allows clinicians to immediately start with higher doses of diuretics without being concerned about the onset of hypotension or blood volume reduction while assessing the patients response to diuretic dosage.

A blood volume control method has been developed including: monitoring a condition of a patient (such as hematocrit (Hct)), wherein the condition is indicative of blood volume in the patient; automatically determining that the condition indicates a low blood volume in the patient; automatically infusing an infusion solution into the patient in response to the determination of a low blood volume, and automatically adjusting the infusion to maintain the monitored condition at a predetermined value. The method may include a transcutaneous hematocrit (Hct) sensor positioned on the skin of a patient, an infusion pump to cause the infusion solution to flow from a solution container, through a tube to a catheter inserted in a vein of the patient and a controller for adjusting the infusion pumping rate to maintain the monitored condition at or near the predetermined value. The infusion pump may be adjusted by repeatedly ceasing and restarting infusion and/or adjust a rate of infusion.

A blood volume control system has been developed comprising: a Hct sensor connected to a patient, measuring a Hct of blood in the patient; an infusion pump connectable to fluid tube for providing fluid communication of a source of an infusion solution to a venous system of a patient via a catheter; a controller receiving a signal from the Hct sensor, wherein the signal is indicative of the Hct and generating a control signal for the infusion pump, wherein the controller actuates the pump in response to an indication from the Hct sensor of a low Hct. The controller may actuate the pump to infuse the infusion solution into the patient at a rate required to maintain a current Hct at or near a predefined Hct target. The infusion pump may cause the infusion solution to flow from a solution container, through a tube to a catheter inserted in a vein of the patient.

A method for controlling a patients Hct using a Hct sensor and an infusion pump has been developed included the steps of: sensing an actual Hct of blood in a vascular system of a patient; comparing the actual Hct to a threshold Hct, and automatically infusing an infusion solution to the patient if the difference between actual Hct and threshold Hct exceed a predetermined level. The method may include adjusting a rate of infusion from a first rated to a slower rate above a zero rate to reduce the difference.

A method of preventing vascular volume depletion using a Hct sensor and an infusion pump, said method comprising: determining a current Hct of blood in a patient; comparing the current Hct to a desired Hct value; infusing an infusion solution to a venous system of the patient if the current Hct is below the desired Hct target value, and infusing the infusion solution into the patient at a rate determined to maintain the desired Hct target value. The current Hct may be monitored by a sensor sensing a translucent property of blood in a surface peripheral venous system of the patient. By maintaining a desired Hct value the vascular volume in the patient may be held to a relatively constant value.

A method of preventing vascular volume depletion during diuretic delivery using a Hct sensor, an infusion solution, an infusion pump and catheter, said method comprising: measuring the current Hct of blood in a patient; an infusion pump connected to the vascular system of the patient, and infusing a volume expansion solution into the vascular space at a rate required to main a Hct target.

DETAILED DESCRIPTION

A closed loop system for the prevention of vascular volume depletion has been developed which is used in conjunction with diuretic therapy in order to ensure the net fluid removed for a patient matches the patients PRR preventing blood volume depletion. The disclosed system in an exemplary embodiment and reacts to increases in Hct to maintain blood volume.

Figure 1:
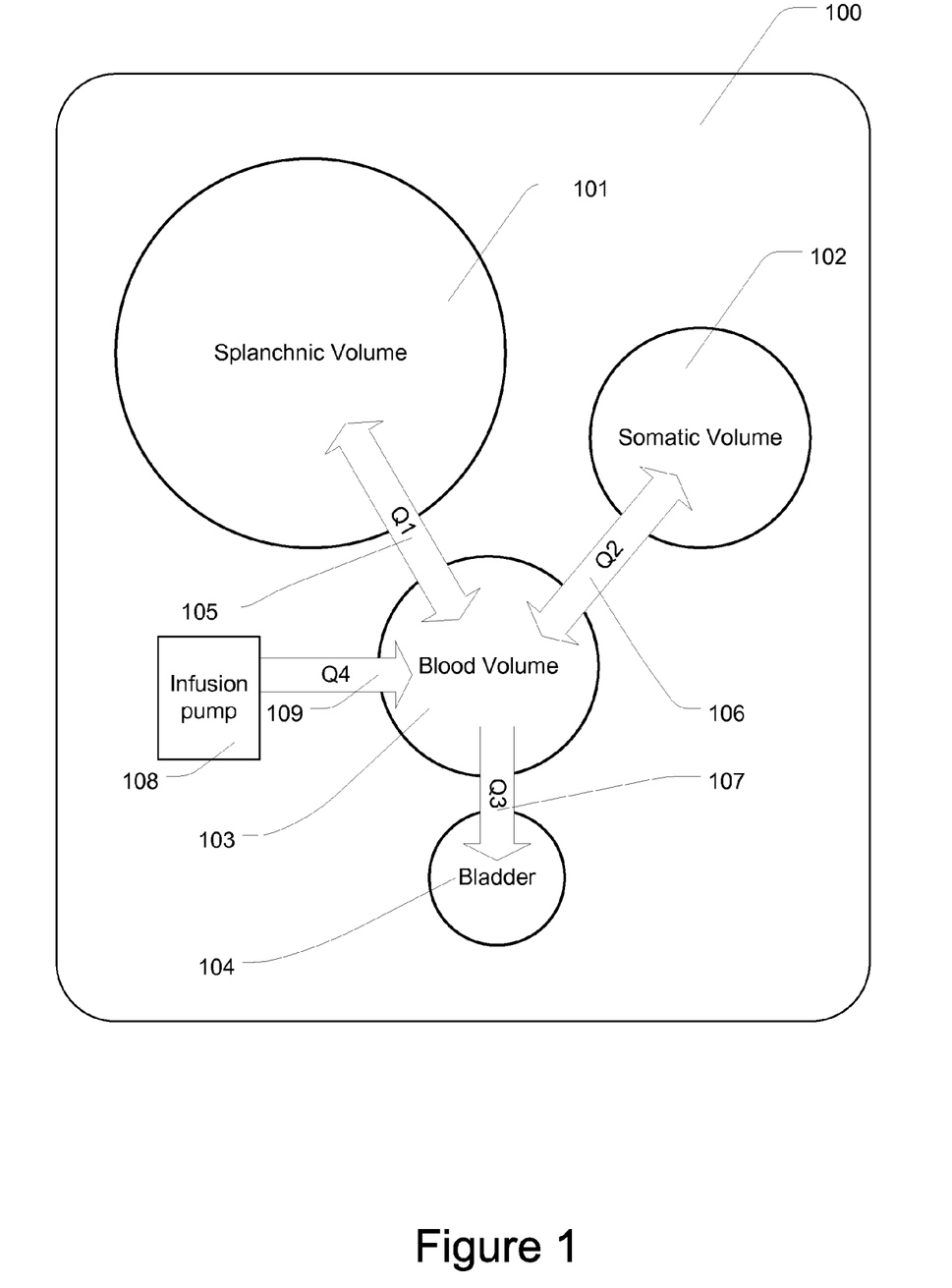
FIG. 1 is a schematic diagram of a model of fluids in a patient.

FIG. 1 shows a four pool body fluid model 100 of an exemplary human body showing extracellular space of the splanchnic and of the somatic volume model of a patient. The model shows how vascular volume is replaced by extra vascular volumes during diuresis. The splanchnic volume 101 (approx 30 liters) and somatic volume 102 (approx 11 liters) feed into the blood volume 103 of approximately 6 liters. Flow Q1 105 indicates the flow of filtrate from the splanchnic volume to the blood volume. Flow Q2 106 indicates the flow of filtrate from the somatic volume to the blood volume and Flow Q3 107 indicates the flow of urine delivered to the bladder 104. If, $Q1+Q2<Q3$ then the blood volume will drop and the potential for hypotension and activation of the RAAS system arises. An extracorporeal infusion pump 108 is controlled such that its infusion flow rate Q4 109 matches the difference between the urine production Q3 107 and plasma refill rate (Q1+Q2). Preferably, the infusion flow rate balances the flows as follows: $Q1+Q2+Q4=Q3$. Thus urine production will be greater than the replenishment solution flow rate, i.e. $Q3>Q4$, and the net fluid loss to the patient will be $Q3-Q4=Q1+Q2$.

Figure 2:
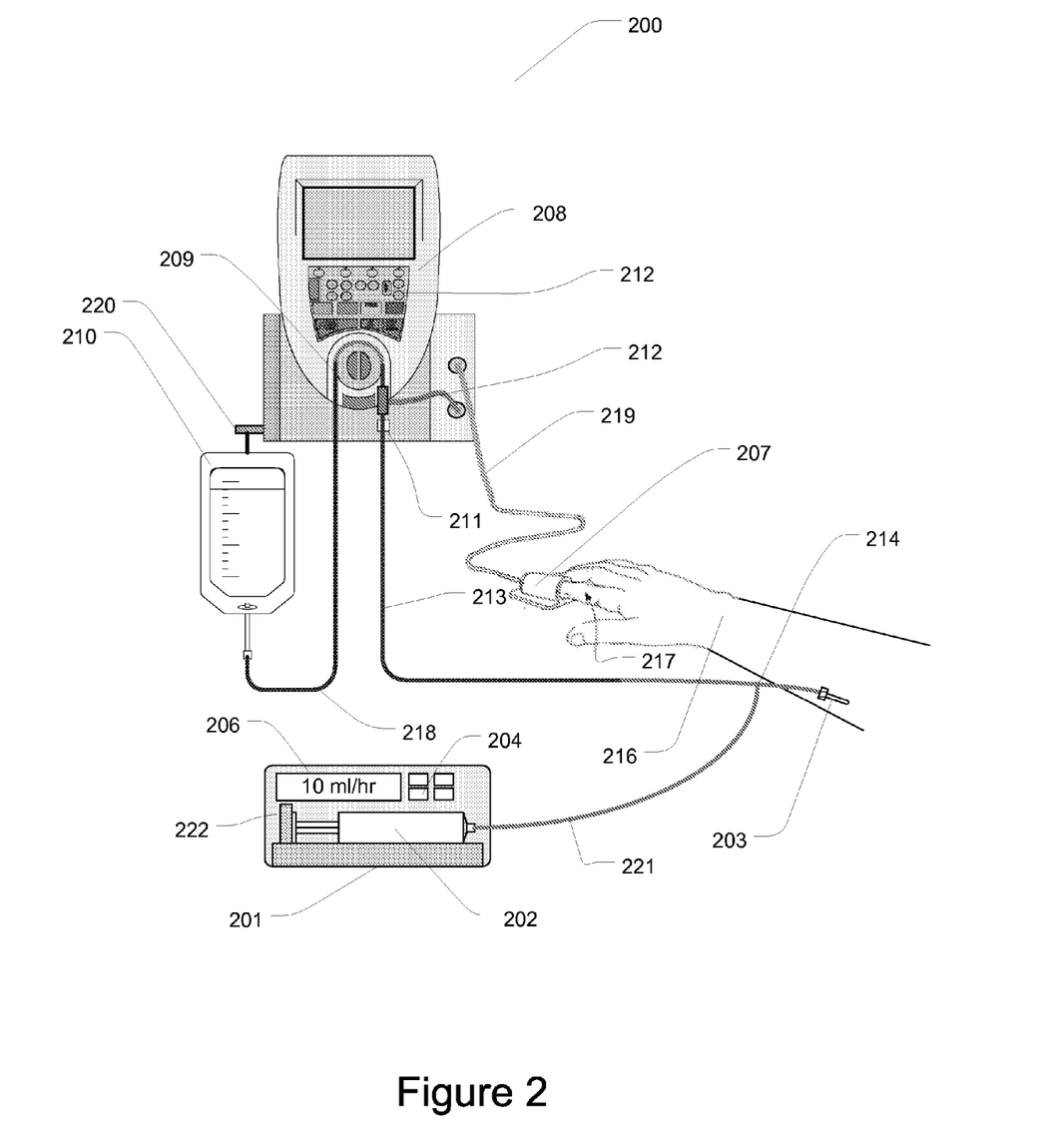
FIG. 2 is a diagram of an exemplary fluid infusion system with a controller for monitoring and responding to Hct levels.

FIG. 2 shows a diagram of the proposed closed loop control system 200 including plant and controller for preventing hypotension and matching PRR to urine output by supplementing vascular volume reductions with automatic infusion of a replacement solution to the blood volume. The patient may be given an oral dose or an intravenous bolus of diuretic or a continuous intravenous drug infusion of a diuretic.

FIG. 2 shows a syringe pump 201 with a continuous intravenous drug infusion of furosemide 202, a common diuretic. The infusion of the drug is achieved via the displacement of the syringe 222 through a conduit tube 221, through IV needle 203 in the patients' peripheral blood vessels in the forearm 216. Access may also be achieved centrally in the venous system, if desired. The user sets the infusion rate and volume to be delivered by syringe pump 201 via the membrane panel 204. The set rate and volume are displayed on the syringe pump LCD 206.

At the same time the patient receives the diuretic, the Hct of the patient may be measured invasively or non-invasively. FIG. 2 depicts the non-invasive measurement of Hct via a finger probe 207 connected to one of the patients' fingers 217. Hct is a measurement of the proportion of the red blood cell volume to whole blood volume. Since the number of red blood cells within the vascular volume is not expected to change significantly over a few days assuming the patient is not hemorrhaging or has a red cell blood disorder, the proportion of red blood cells is an excellent indicator of blood volume changes. If the Hct remains constant, it is safe to assume that the blood volume has remained constant. Such Hct measurement devices are available commercially from companies such as Hemametrics Inc. The processing system for the Hct sensor 207 is contained within the console housing 208 and an electrical connection is made between the sensor and console via the cable 219.

If the measured Hct rises above the designated Hct target which may be higher or lower than the base Hct of the patient, replenishment solution is delivered to the patients' vascular space. The replenishment infusion pump 209 is part of the console 208 and withdraws replenishment solution from a fluid bag 210 via a conduit tube 218 with the peristaltic pump 209. The peristaltic pump 209 propels the replenishment solution through an ultrasonic air detector sensor 211 and inline pressure sensor 212 via a conduit tube 213 and into the patient through an IV catheter 203. The conduit tubing 213, 218, 221 may be made from silicone, PVC or polyurethane or other such suitable medical grade material. The air detector detects 211 bubble in the range of 50 uL and the pressure transducer measures pressures in the range of –400 to 600 mmHg. The pressure sensor is used for the detection of occlusions and disconnects which may occur during therapy. Since the infusion system is connected to the patient's venous system, which is typically pressurized in heart failure patients between 3 and 20 mmHg, the potential for blood loss if small, given the resistance of 18 to 22 G IV needles in the event of a disconnect. The IV diuretic infusion system and replenishment solution infusion system are connected via a T-connector 214 before the combined fluid is infused into the patient. Such a connection can be made to minimize the number of connections to the patient but is not necessary. Alternatively two IV cannulae may be used independently.

The replenishment infusion pump is capable of infusion flow rates of 0 to 100 ml/min in increments as low as 0.1 ml/hr. The replenishment solution bag 210 may be attached to a weigh scale 220 to independently check the flow of the peristaltic pump 209 by examining the change in weight over time and for determining when the replenishment solution bag is empty. Replenishment solution bags may be of 0.5 liters to 6 liters in volume. In the event that the weight scale 220 fails to alarm, the air detector 211 will detect the presence of air when the replacement solution bag is empty or the infusion pressure sensor will detect a drop in pressure and the console will alarm for a circuit disconnect. The infusion pump is stopped in the event of air being detected within the circuit with the air detector, the weight of the replacement solution bag is below a limit or the circuit becoming disconnected from the patient. In order to prevent nuisance alarms the infusion pressure is also actively controlled to ensure it does not exceed pressures exceeding 350 mmHg as to actively limit pressure excursions and limit the potential for extravasation.

The consoles control processor reads the patient's Hct at a predefined cycle time, and adjusts the infusion rate of replenishment solution based upon the error between the desired Hct and the actual Hct reading. If the Hct reading is above the TargetHct setting replenishment solution is delivered and if it is below the TargetHct infusion of replenishment solution is ceased. The TargetHct setting may be set based upon the base Hct reading of the patient or at some level higher or lower than the base reading. If the Hct target is set higher than the base reading it means that some level of blood volume reduction is acceptable and if it is set lower than the base reading it means that some level of blood volume expansion is acceptable.

The Hct target setting is input via the console membrane panel 221 using the LCD 222 as visual feedback. Upper and lower Hct alarm limits may also be set via the membrane panel to alert the user to a potential problem in patient volume status. If either limit is exceeded the peristaltic pump is stopped by the console processor and an alarm is annunciated both audibly and visually. The PRR rate may also be increased artificially by the infusion of a HSS (Hypertonic Saline Solution) or other such blood volume expander such as a dextrose solution, sodium bicarbonate solution or albumin using a standard syringe and IV needle. The increased oncotic pressure caused by the plasma expander within the vascular space helps to recruit fluid from the splanchnic and somatic volume increasing the patient's ability to diurese. Upper limits for the replacement solution maximum flow rate and volume may also be set via the membrane panel and LCD. The plasma expander may also be delivered as part of the replenishment solution or independently as a bolus or continuous drip.

Figure 3:
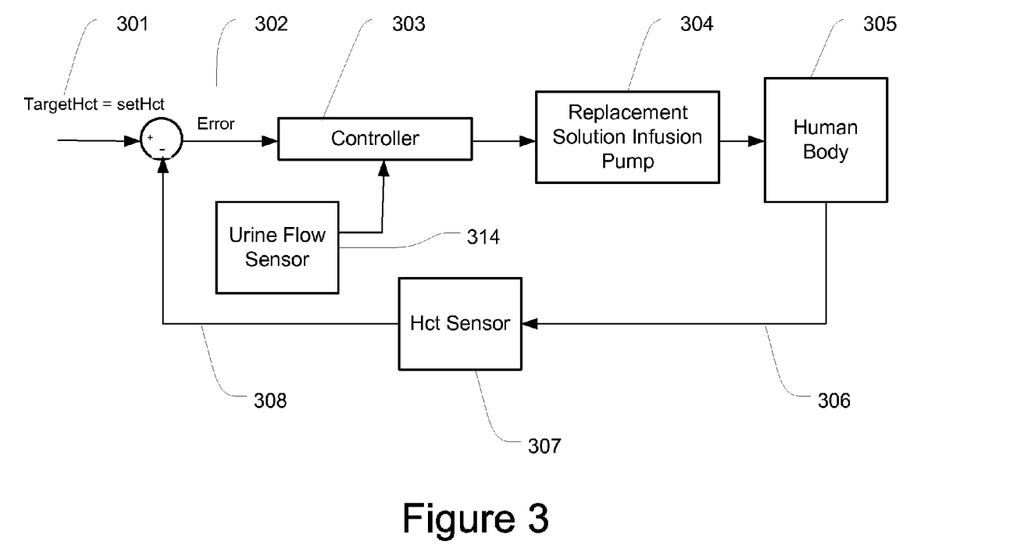
FIG. 3 is a controller flow chart.

FIG. 3 shows a flow chart of a controller for controlling Hct. The Measured Hct Signal 308 measured using the Hct sensor (FIG. 2, 207) is subtracted from a TargetHct set point 301. The error (difference between TargetHct and Measured Hct) 302 is fed to a controller 303 that adjusts the infusion of replenishment fluid to eliminate this error. The controller 303 may adjust the replenishment flow only when the error is positive. The controller also limits the infusion flow rate based upon the user set limit of 1 to 300 ml/min for infusion. If the controller rate is greater than this preset flow limit, the output of the controller is limited to a maximum of this user set limit.

The controller 304 commands the replacement solution pump 304 (FIG. 2, 209) to deliver replenishment solution at the rate determined by the controller. When the replenishment solution is infused via an IV needle into the patient 30, the Hct level in the vascular system is modified. The change 306 in Hct is detected by the Hct sensor 307. The sensor signal is again fed back 308 to the error calculation 302, and the process continues at the controller cycle rate. Since the replenishment solution rate on average should never exceed the urine production rate, a further enhancement is to measure 314 the urine production level and limit the flow and volume of the replenishment solution to some predetermined proportion of the urine flow and volume production level. In other words, if the urine production is excessive the infusion of the replenishment solution is reduced or stopped.

Figure 4:
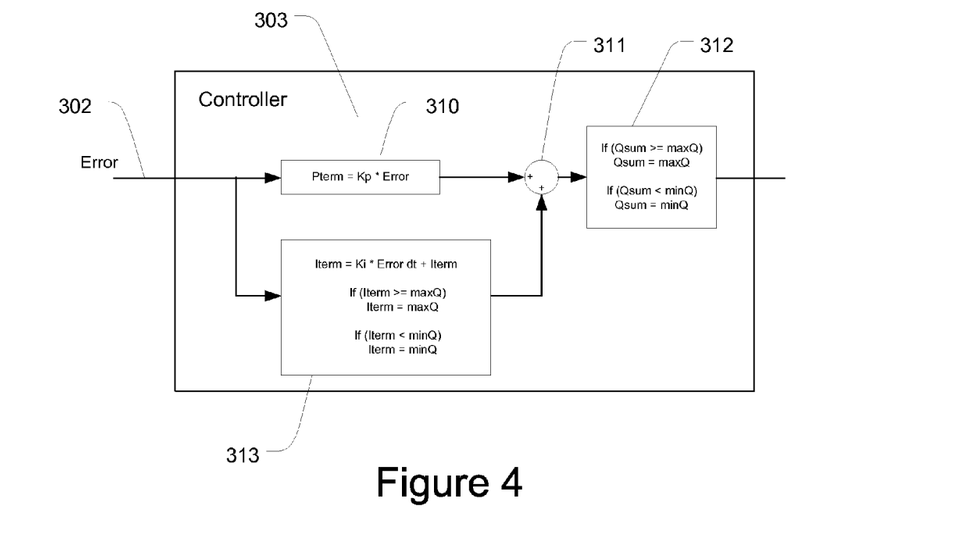
FIG. 4 is a schematic diagram of a system to provide Hct control.

FIG. 4 shows a flow chart of the controller 303 used to determine the replenishment solution flow rate. The controller may include a PI (Proportional Integral) controller with anti-windup protection on the integrator. The proportional term is calculated by multiplying the Hct error 302 by the proportional gain Kp 310. The integral term (Iterm) is calculated multiplying the Hct error 302 by the integral gain Ki 313 and adding the output to the previous integral term (Iterm). The Iterm is limited by the allowable maximum and minimum replenishment solution flow rates maxQ and minQ respectively. The minimum replenishment rate, minQ is 0 ml/min and the max replenishment rate, maxQ is defined by the user via the console user interface. The proportional and integral terms are summed to Qsum, 311 and the resultant output is again bounded by maxQ and minQ 312 before the pump is commanded with the resultant Qsum replenishment solution flow rate.

Figure 5:
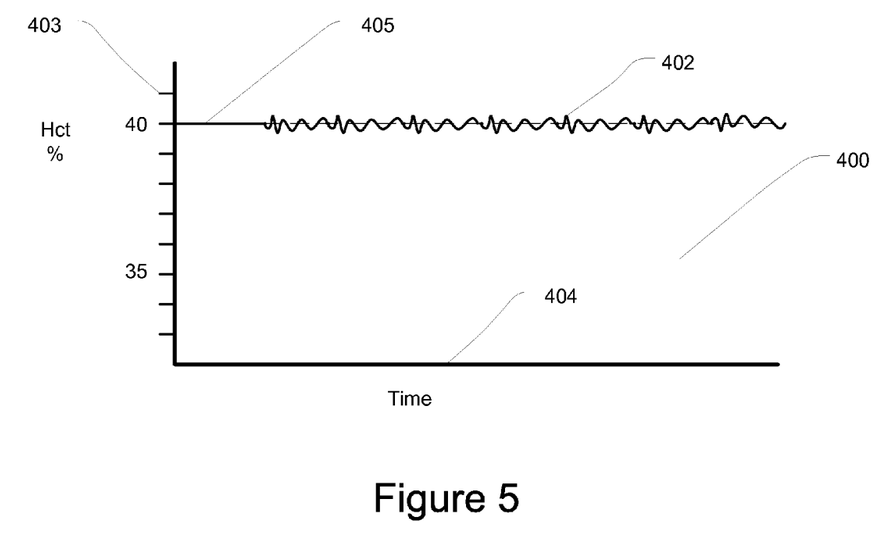
FIG. 5 is a graph of Hct verses time during diuretic control.

FIG. 5 shows a graph of the variance in Hct and infusion rate of the replenishment solution over time during a therapy. FIG. 5 400 shows time 404 versus the patient's Hct in terms of percent 403. The TargetHct 405 was set to 40% as denoted by the straight horizontal line. The measured Hct 402 is shown to be controlled within close proximity to the TargetHct.

Figure 6:
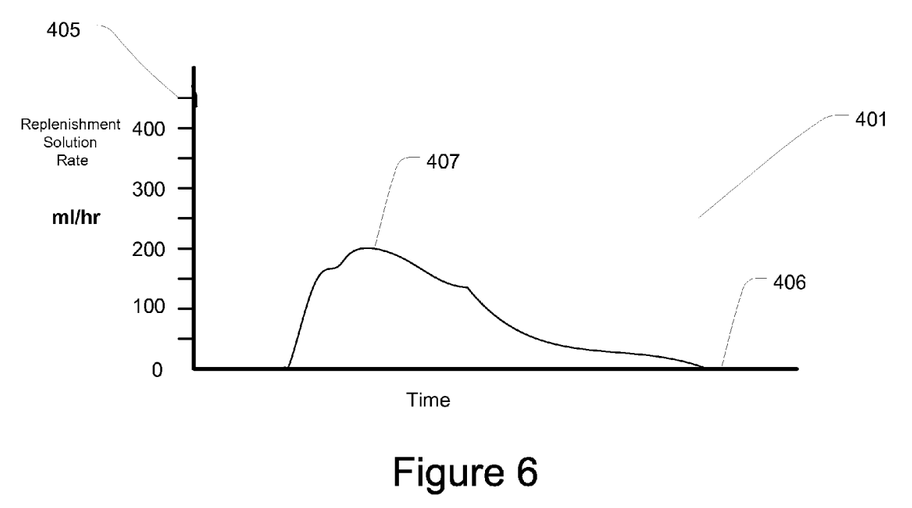
FIG. 6 is a graph of replenishment solution verses time during diuretic control.

FIG. 6 401 shows a graph of time 406 Vs the replenishment solution rate 405 in ml/min. In this case shown in FIG. 4, a bolus of furosemide was delivered to the vascular system of the patient. It took over an hour before the drug took effect and when it did the patient urinated at a rate that exceed the PRR. The replenishment solution flow rate 407 was delivered at a rate determined by the Hct controller to main the TargetHct. The replenishment flow rate rapidly increased to compensate for the excessive urine flow due to the diuretic. The effect of the diuretic diminished over time and the replenishment solution was eventually stopped while Hct remained constant. This prevented hypotension and the resulting activation of the neurohumoral axis.

The invention has been described in connection with the best mode now known to the applicant inventors. The invention is not to be limited to the disclosed embodiment. Rather, the invention covers all of various modifications and equivalent arrangements included within the spirit and scope of the appended claims.

What is claimed is:

1. A blood volume control method comprising:
   repeatedly monitoring and measuring a hematocrit (Hct) level of blood of a patient;
   repeatedly determining a difference between the measured Hct level and a predetermined Hct level;
   in response to a determination that the difference exceeds a predetermined value, automatically infusing an infusion solution into the patient to decrease the Hct level by increasing the blood volume in the patient,
   continuing to automatically infuse the solution while the difference exceeds the predetermined value,
   reducing or ceasing the automatic infusion of the solution while the difference is at or below the predetermined value, and
   monitoring urine output of the patient, and reducing or ceasing the automatic infusion of the infusion solution while the urine output is above a predetermined threshold level of urine output.

2. A blood volume control method as in claim 1 wherein the Hct level is monitored by a transcutaneous hematocrit (Hct) sensor.

3. A blood volume control method as in claim 1 wherein the Hct level is monitored by a sensor sensing a translucent property of blood in a surface peripheral venous system of the patient.

4. A blood volume control method as in claim 1 wherein an infusion pump causes the infusion solution to flow from a solution container, through a tube to a catheter inserted in a vein of the patient.

5. A blood volume control method comprising:
   repeatedly monitoring and measuring a hematocrit (Hct) level of blood of a patient;
   repeatedly determining a difference between the measured Hct level and a predetermined Hct level;
   in response to a determination that the difference exceeds a predetermined value, automatically infusing an infusion solution into the patient,
   continuing to automatically infuse the infusion solution while the difference exceeds the predetermined value,
   automatically ceasing or reducing a rate of the infusion of the infusion solution in response to the difference being no greater than the predetermined value;
   monitoring urine output of the patient, and
   reducing or ceasing the infusion of the infusion solution if the monitored urine output is less than a predetermined threshold level of urine output.

6. A blood volume control system comprising:
   a Hct sensor connected to a patient measuring a Hct of blood of the patient;
   a urine flow sensor monitoring urine output by the patient;
   an infusion pump connectable to a fluid tube providing an infusion solution from a source of the infusion solution to a venous system of a patient;
   a controller receiving a Hct signal indicating a Hct level of the blood from the Hct sensor and a urine signal from the urine flow sensor indicating a urine output rate, the controller:
   repeatedly determines a Hct difference between the Hct level indicated by the Hct signal and a threshold Hct level;
   while the Hct difference exceeds a predetermined value, automatically actuating the pump to infuse an infusion solution into the patient to reduce the Hct level by increasing blood volume in the patient,
   reducing a rate of infusion or stopping the infusion in response to the Hct difference being no greater than the predetermined value, and
   monitoring urine output of the patient, and actuating the pump to stop or reduce the infusion of the infusion solution if the urine output is above a predetermined threshold urine output.

7. A blood volume control system as in claim 6 wherein the Hct sensor senses a translucent property of blood in a surface peripheral venous system of the patient.

8. A blood volume control method as in claim 6 wherein the infusion pump causes the infusion solution to flow from a solution container, through a tube to a catheter inserted in a vein of the patient.

9. A method for controlling a Hct level of blood in a patient using a Hct sensor and an infusion pump, said method comprising:
   repeatedly sensing current Hct level of blood of a vascular system of the patient;
   repeatedly determining a difference between the sensed Hct level and a predetermined threshold Hct level;

monitoring urine output of the patient and determining whether the monitored urine output is above a predetermined threshold urine output;

automatically increasing an infusion rate of an infusion solution to the patient while the difference between the sensed Hct level and the threshold Hct level is above a predetermined difference value;

automatically reducing the infusion rate or ceasing the infusion of the infusion solution while the difference is less than a predetermined value;

automatically reducing the infusion rate or ceasing the infusion of the infusion solution while the monitored urine output is above a threshold urine output.

10. A method as in claim 9 further comprising adjusting a rate of infusion from a first rate to a slower rate above a zero rate to reduce the difference.

11. A method of preventing vascular volume depletion using a Hct sensor and an infusion pump, said method comprising:

repeatedly determining a Hct of blood of a patient;

repeatedly comparing the Hct to a predetermined desired Hct value;

monitoring urine output of the patient;

infusing an infusion solution to a venous system of the patient while the Hct is above the desired Hct target value and the monitored urine output is below a threshold urine output level;

reducing the infusion rate or stopping the infusion in response to the Hct becoming less than the Hct target value, and reducing the infusion rate or stopping the infusion in response to the urine output becoming greater the threshold urine output.

12. A method as in claim 11 wherein the Hct is monitored by a sensor sensing a translucent property of blood in a surface peripheral venous system of the patient.

13. A method as in claim 11 wherein the infusion causes the infusion solution to flow from a solution container, through a tube to a catheter inserted in a vein of the patient.

14. A method as in claim 11 further comprising at least temporarily ceasing the infusion after the monitored urine output is above the threshold urine output level.

15. A method as in claim 11 wherein the rate is a variable rate adjusted to maintain a constant vascular volume in the patient.

16. A method of preventing vascular volume depletion during diuretic delivery using a Hct sensor, an infusion solution, an infusion pump and catheter, said method comprising:

repeatedly sensing a current Hct level of blood of a patient;

comparing each of the sensed current Hct levels to a target Hct level, repeatedly sensing current urine output level of the patient;

comparing each of the sensed current urine output levels to a target urine output level, and actuating the infusion pump to infuse a solution into the vascular space while the sensed current Hct level is above the target Hct level;

stopping the infusion pump or reducing a rate of infusion of the solution in response to the current Hct level falling below the target Hct level, and stopping the infusion pump or reducing a rate of infusion of the solution in response to the current urine output level exceeding a target urine output level.

17. A method as in claim 16 wherein the infusion pump causes the solution to flow from a solution container, through a tube to a catheter inserted in a vein of the patient.

18. A method as in claim 16 wherein the rate is a variable rate adjusted to maintain a constant vascular volume in the patient.

19. A method as in claim 16 wherein the current Hct level is monitored by a sensor sensing a translucent property of blood in a surface peripheral venous system of the patient.

* * * * *